US006820612B2

(12) United States Patent
Harabin

(10) Patent No.: US 6,820,612 B2
(45) Date of Patent: Nov. 23, 2004

(54) INHALER HOLSTER

(76) Inventor: Robin Harabin, 261-B W. Main St., Bound Brook, NJ (US) 08805

( * ) Notice: Subject to any disclaimer, the term of this patent is extended or adjusted under 35 U.S.C. 154(b) by 0 days.

(21) Appl. No.: 10/102,328

(22) Filed: Mar. 21, 2002

(65) Prior Publication Data

US 2003/0178023 A1 Sep. 25, 2003

(51) Int. Cl.$^7$ ............................................. A61M 11/00
(52) U.S. Cl. .............................. 128/200.23; 128/203.15
(58) Field of Search ................... 128/200.24, 200.14, 128/200.21, 200.23, 203.12, 203.15, 203.23, 200.12, 912, 205.22, 200.18; 224/217–219, 237, 250, 255, 269, 267, 148.6, 901, 901.2, 901.6; 222/175.3, 172, 160, 183, 153.01, 153.11; D3/203, 22.15, 218, 222, 228, 215

(56) References Cited

U.S. PATENT DOCUMENTS

| | | | |
|---|---|---|---|
| 4,023,712 A | | 5/1977 | Babiak et al. ............... 222/175 |
| 4,106,698 A | | 8/1978 | Lin ............................ 239/34 |
| 4,114,811 A | | 9/1978 | Loeffler ..................... 239/288.5 |
| 4,420,076 A | | 12/1983 | Beveridge et al. ............ 206/37 |
| 4,454,966 A | * | 6/1984 | Hicks ..................... 222/153.11 |
| 4,463,879 A | * | 8/1984 | Des Voignes ............... 222/175 |
| 4,756,407 A | | 7/1988 | Larsen ......................... 206/37 |
| 4,765,459 A | | 8/1988 | Edwards .................... 206/38.1 |
| 4,817,822 A | | 4/1989 | Rand et al. .................... 222/38 |
| 4,849,948 A | | 7/1989 | Davis et al. .................. 368/10 |
| 5,058,405 A | | 10/1991 | Stillwagon ................ 70/456 R |
| 5,088,624 A | | 2/1992 | Hackett et al. ............... 222/78 |
| 5,111,968 A | | 5/1992 | Wilkerson .................... 222/47 |
| 5,148,949 A | * | 9/1992 | Luca ........................... 222/175 |
| 5,209,090 A | | 5/1993 | Stillwagon ................ 70/456 R |
| 5,215,227 A | * | 6/1993 | Farner ......................... 222/175 |
| 5,287,995 A | * | 2/1994 | Redman et al. ............. 222/175 |
| 5,443,192 A | * | 8/1995 | Hodges et al. ............ 224/148.6 |
| 5,477,999 A | * | 12/1995 | Blankenship ............... 224/253 |
| 5,511,538 A | | 4/1996 | Haber et al. ............ 128/200.14 |
| 5,531,359 A | * | 7/1996 | Winner ..................... 222/153.11 |
| 5,544,647 A | | 8/1996 | Jewett et al. ............ 128/200.23 |
| 5,570,817 A | * | 11/1996 | Anderson et al. ......... 222/153.11 |
| 5,582,164 A | * | 12/1996 | Sanders .................. 128/205.22 |
| 5,602,802 A | | 2/1997 | Leigh-Spencer et al. ...... 368/10 |
| 5,622,163 A | | 4/1997 | Jewett et al. ............ 128/200.23 |
| 5,709,320 A | * | 1/1998 | Jimenez ....................... 222/175 |
| 5,730,118 A | | 3/1998 | Hermanson ............ 128/200.14 |
| 5,755,221 A | | 5/1998 | Bisgaard ................ 128/203.15 |
| 5,810,886 A | | 9/1998 | Hassan ......................... 606/234 |
| 5,833,093 A | | 11/1998 | Honaker et al. ............. 222/175 |
| 5,855,307 A | | 1/1999 | Biddick et al. .............. 224/267 |
| 5,875,945 A | * | 3/1999 | Roach ......................... 224/217 |
| 5,899,200 A | | 5/1999 | McNary ................ 128/200.14 |
| 5,909,822 A | | 6/1999 | George et al. ................ 221/25 |
| 5,915,560 A | | 6/1999 | George et al. .............. 206/537 |

(List continued on next page.)

*Primary Examiner*—Henry Bennett
*Assistant Examiner*—Teena Mitchell
(74) *Attorney, Agent, or Firm*—Ernest D. Buff & Associates, LLC; Ernest D. Buff; Mark J. Halvorson

(57) ABSTRACT

An asthma/allergy inhaler holster has a main body part comprising an elongated sheath. A holding mechanism attached proximal to an open end of said main body part, and extending over the open end secures an inhaler within the holster. A grommet is affixed to the main body part and positioned off center proximal to a closed end of the sheath. The grommet is adapted to attach the inhaler holster to a member, such as a key chain, ring, or the like, passed therethrough. The holster substantially envelops the inhaler, to protect it from contamination by dirt and debris. Its construction affords immediate access to the medicament in the inhaler. Adjustment and holding mechanisms cooperate collectively to enable the holster to accommodate differently sized inhalers. The convenience afforded by the grommet decreases difficulties presented when the user forgets the holster during travel away from the home. An empty holster serves to remind the user to replace the inhaler before traveling to a location where asthma/allergy medication is likely to be unavailable.

4 Claims, 4 Drawing Sheets

U.S. PATENT DOCUMENTS

| | | | |
|---|---|---|---|
| 5,961,003 A | * 10/1999 | Coryell | 222/175 |
| D418,389 S | * 1/2000 | Olson | D3/208 |
| 6,112,961 A | * 9/2000 | Phillips | 224/222 |
| 6,126,040 A | * 10/2000 | Hippenstell | 222/78 |
| 6,142,339 A | 11/2000 | Blacker et al. | 222/23 |
| 6,145,654 A | * 11/2000 | Loghman | 206/37 |
| 6,164,275 A | 12/2000 | Van Iderstine | 128/200.14 |
| 6,196,419 B1 | * 3/2001 | Haney et al. | 222/79 |
| 6,199,726 B1 | * 3/2001 | Cardwell, III et al. | 222/402.11 |
| 6,330,430 B1 | * 12/2001 | Jensfelt | 455/575.8 |
| 6,360,929 B1 | * 3/2002 | McCarthy | 224/251 |
| 6,364,187 B1 | * 4/2002 | Castellano et al. | 224/675 |
| D464,793 S | * 10/2002 | Anderton | D3/215 |
| 6,557,737 B1 | * 5/2003 | Hanson | 224/148.6 |
| 6,685,068 B1 | * 2/2004 | Thompson et al. | 224/251 |

* cited by examiner

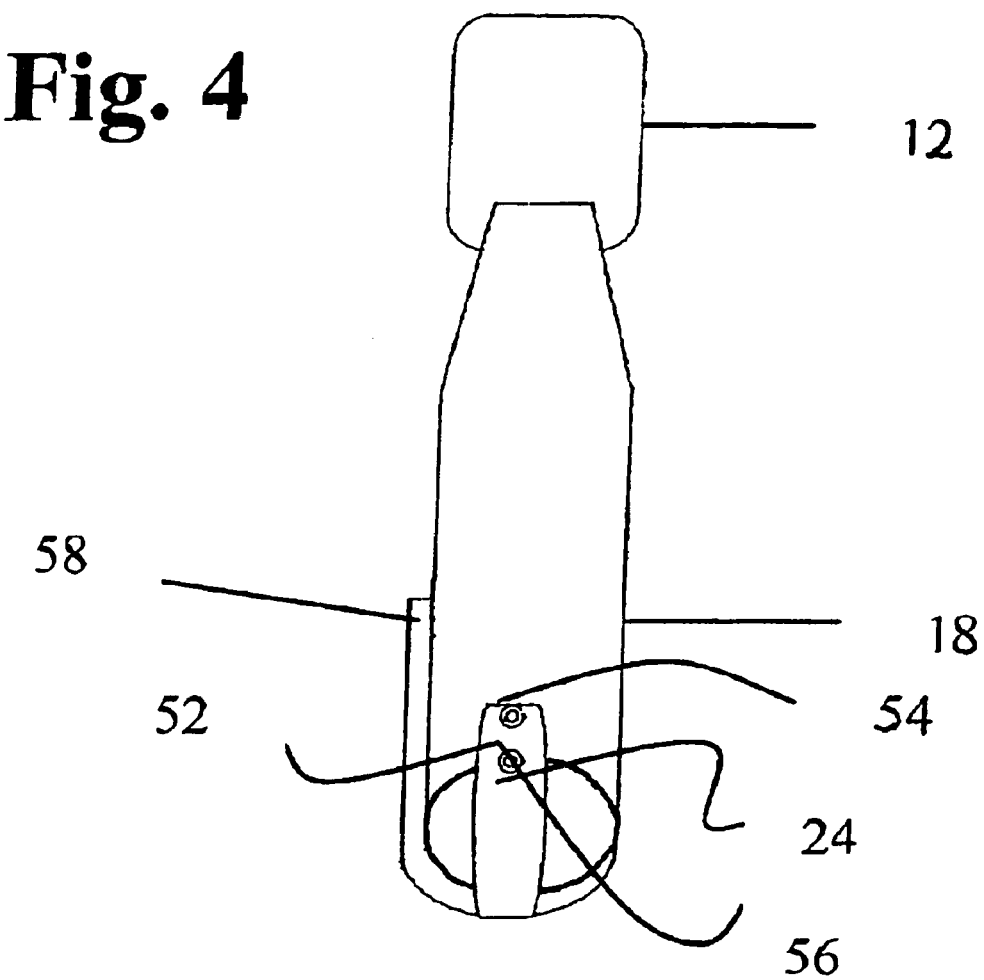

INHALER HOLSTER

BACKGROUND OF THE INVENTION

1. Field of the Invention

The present invention relates to an inhaler carrier for transporting a medical canister that contains an oral or nasal medicament within a plastic actuator; and more particularly to an asthma/allergy inhaler holster that is adapted to be attached to the user's keys, and which has an improved construction operative to provide additional protection for the inhaler while, at the same time, allowing immediate access to the medicament therewithin.

2. Description of the Prior Art

Various carriers for medical canisters are disclosed in the prior art. U.S. Pat. No. 5,833,093 to Honaker et al. discloses a protective cover for small spray dispensers and medicated inhalers. Although this cover can accommodate differently sized inhalers, the user does not have immediate access to the medicament in the inhaler should the need arise. In addition, the inhaler is subject to contamination from dirt and debris while residing in the protective cover. U.S. Pat. No. 5,855,307 to Biddick et al. discloses a container holster that is strapped around a users wrist. An inhaler band wraps around the central region of the inhaler leaving much of the inhaler exposed to dirt and other contaminants. U.S. Pat. No. 6,164,275 to Van Iderstine discloses an inhaler carrier for holding a plastic actuator that encloses a medical canister. The carrier comprises three loops that support and carry the plastic actuator during transport of the inhaler carrier. The carrier does not accommodate differently sized plastic actuators and does not substantially protect the inhaler from being contaminated with dirt and debris.

There remains a need in the art for an inexpensive asthma/allergy inhaler holder that substantially protects the inhaler from being contaminated with dirt and debris and allows immediate access to the medicament in the inhaler.

SUMMARY OF THE INVENTION

The present invention provides an asthma/allergy inhaler holster having an improved constructive operative to provide additional protection to an inhaler. At the same time, the inhaler holster construction affords immediate access to the medicament in the inhaler. A grommet in the holster allows a member passed therethrough to be attached to the holster making it more convenient for the user to carry the holster. The member can be a key chain, ring, gym bag, briefcase, pocket book, back pack and like object to which the user has immediate access. The convenience afforded by the grommet significantly decreases the difficulties presented when the user forgets the holster during travel away from the home. In addition, the holster has an adjustment means and a holding means that cooperate collectively to enable the holster to accommodate differently sized inhalers.

Generally stated, the invention provides a holster that substantially protects an inhaler from contamination while continuing to permit immediate access to the medicament therewithin. In one aspect of the invention, the holster is designed to accommodate a plastic actuator having a removable cap. In another aspect, the holster construction is especially suited to accommodate a plastic actuator having a hinged cap. These plastic actuators, hereinafter referred to, respectively, as the "removable cap embodiment" and "hinged cap embodiment" are prevalent, and commercially available.

Generally stated, the holster comprises an elongated sheath having an open end and a closed end. A holding means located near an open end of the sheath holds the inhaler firmly within the sheath. An adjustment means, present on the removable-cap embodiment extends over the cap and prevents the cap from falling off the inhaler. A grommet is located off-center near the closed end of the sheath, allowing a user to activate the inhaler without removing the inhaler from the holster. The grommet is used to attach a member passed therethrough to the holster. The member can comprise a (i) key chain, (ii) key ring, (iii) belt loop on a purse, briefcase, gym bag or backpack, and like objects to which the user will likely have immediate access.

Preferably, the holding means includes one or more strips of hook and loop fasteners. An adjustment means comprising snap fastening means is provided. The holster is composed of vinyl or soft leather.

The present invention provides, in combination, an asthma/allergy inhaler holster in which the holster substantially envelops the inhaler, thereby preventing dirt and debris from contaminating the inhaler and fouling movable components. Utilization of the inhaler is facilitated, with the result that the inhaler can be used in the "holstered" condition. The holster is generously sized and includes an adjustment means that enables it to accommodate inhalers having a variety of different shapes and sizes. Removal of the inhaler from the holster to provide for maximum airflow and enhanced pumping action is easily accomplished. The inhaler can be readily removed from the holster by a one-hand operation.

The asthma/allergy inhaler holster of this invention is inexpensive to construct and reliably holds and protects a myriad of differently sized plastic actuators. Unlike conventional inhaler carriers, the asthma/allergy inhaler holster substantially envelops the plastic actuator, to protect the inhaler against contamination from dirt and debris which, if present, might be inhaled during use of the inhaler. The holster is especially suited to be attached to a key ring, key chain, gym bag, briefcase, pocket book, backpack and like objects to which the user has immediate access. Inasmuch as the user will likely remember, or require, his keys, gym bag, briefcase, pocket book, backpack or like object to which the holster is regularly attached when traveling away from the home, the inhaler is liable to be available in the event of an emergency when the medicament is needed. An empty holster reminds the user to replace the inhaler before traveling to a location where asthma/allergy medication is likely to be unavailable. The presence of the holster flags medical personnel, focusing attention on potential asthmatic conditions to aid rescue efforts during asthmatic emergencies.

BRIEF DESCRIPTION OF DRAWINGS

The invention will be more fully understood and further advantages will become apparent when reference is had to the following detailed description and the accompanying drawings, in which:

FIG. 4 is a frontal view of the hinged-cap embodiment of the holster showing the fastening means.

DESCRIPTION OF THE PREFERRED EMBODIMENTS

The present invention provides an asthma/allergy inhaler holster 10 having a construction that advantageously provides substantial protection for an inhaler 30, while continuing to allow immediate access to the medicament in the inhaler. The inhaler 30 comprises a canister containing a plastic actuator within which the medicament is enclosed.

Figure 1:
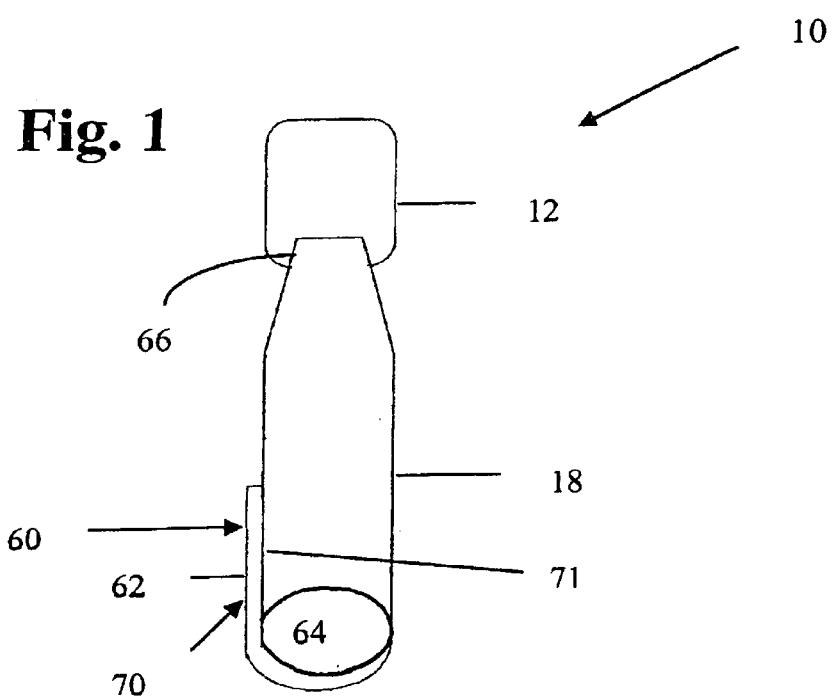
FIG. 1 is a frontal view of an inhaler holster of the invention.
Figure 3:
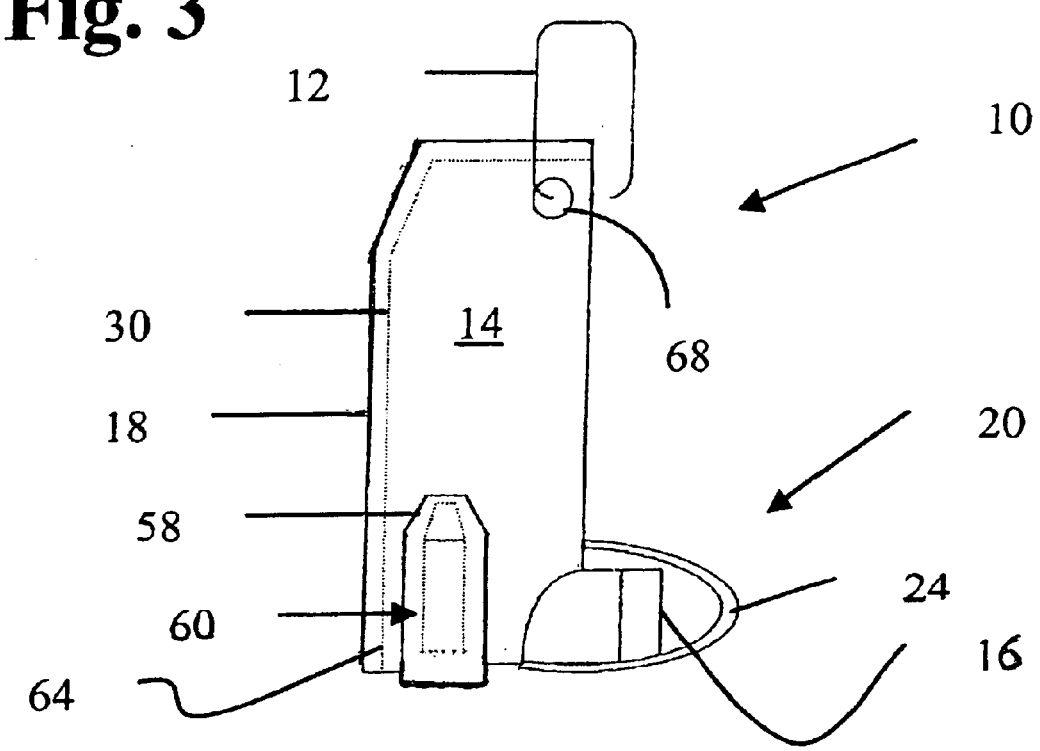
FIG. 3 is a side view depicting the hinged-cap embodiment of the holster, having an inhaler therein.

In FIG. 1 there is shown the asthma/allergy inhaler holster of the present invention. The holster 10 is comprised of a piece of material that is convexly folded to form a sheath 18 having an open end 64 and a closed end 66. A grommet, shown at 68 in FIG. 3, is located off-center proximal to the closed end of the sheath 18, and can be used to attach the holster 10 to a user's key ring 12, or to a pocket book, belt loop, book bag, necklace or the like. The grommet 68 is positioned to allow a user to actuate the inhaler 30 without removing the inhaler 30 from the holster 10. A holding means 60 located proximal to open end 64 secures the inhaler 30 within the sheath 18.

Figure 2:
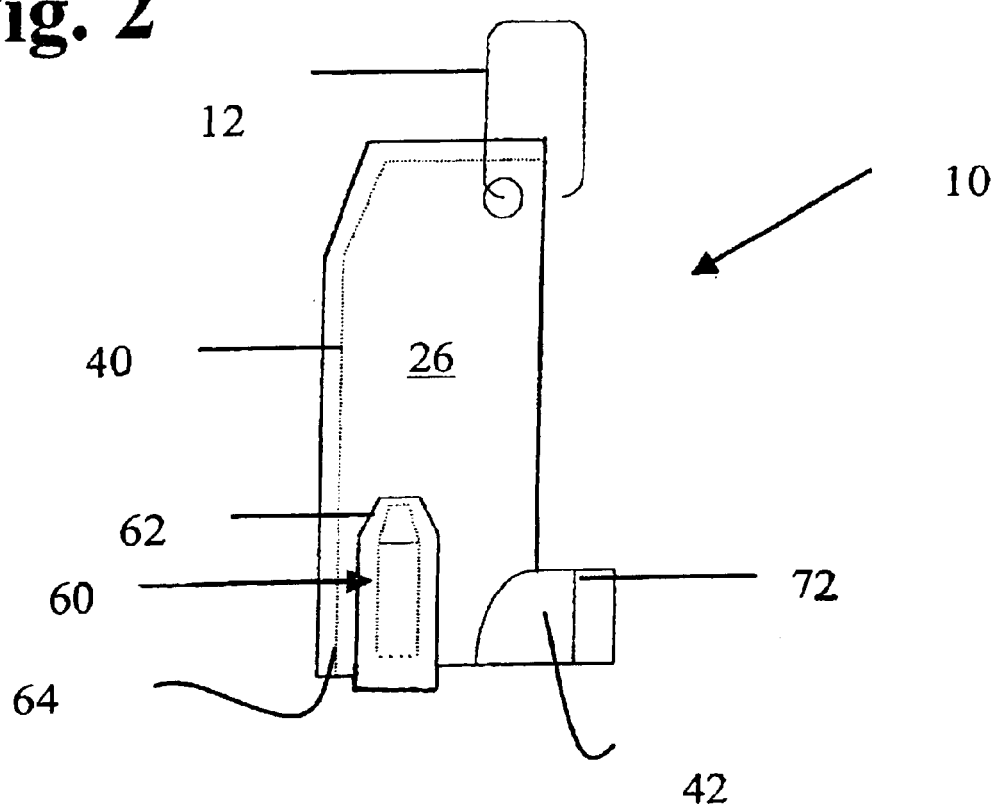
FIG. 2 is a side view depicting the removable cap embodiment of the holster, having an inhaler therein.

As best shown by FIG. 1, the holding means 60 comprises a first strap 62 that runs transverse to the top of the holster 10 with one end of the first strap reversibly attached to the sheath 18 by an attachment means 70. The attachment means 70 comprises one or more strips of hook and loop fasteners known as VELCRO®. The attachment means 70 has a hooked portion located on the sheath extending longitudinally thereof, and a loop portion located on the underside of the first strap 62. The arrangement of the attachment means 70 permits the strap 62 to be readily adjusted so that varying sizes of plastic actuators are reliably held within the sheath 18. In FIG. 2 a first plastic actuator 26 with hinged cap 42 is located within the sheath 18 of the holster 10, secured by the holding means 60 of the holster 10. The hinged cap 42 can be removed from mouth 72 of the first plastic actuator without having to pull off the holding means 60, thereby allowing a user immediate access to the medicament in the inhaler 30. For maximum airflow and enhanced pumping action, the strap 62 is readily disengaged to permit removal of the inhaler from holster 10.

Referring to FIG. 3, there is shown another embodiment of the holster 10. In the embodiment shown, a second plastic actuator 14 having a removable cap 16 is located within the sheath 18. The holding means 60 of this removable cap embodiment comprises the first strap 58 that secures the inhaler within the elongated sheath and a second strap 24 that is adapted to extend over the removable cap 16 and can be attached to the holster by a suitable fastener means. The second strap 24 is perpendicularly attached to the first strap and runs transverse to the removable cap 16, holding the removable cap onto the mouth of the second plastic actuator 14. The second strap 24 is reversibly attached to the sheath 18 using a suitable fastening means. Preferably, the fastening means comprises a plurality of female snap fastener elements and a male snap fastener element. Female snap fastener elements 52, 54 are longitudinally disposed on the second strap 24, and are adapted to selectively and releasably mate with a single male snap fastener element 56 fixedly attached to the sheath 18. This combination of multiple female snap fastener elements 52, 54 allows the holster to accommodate differently sized inhalers. The fastening means 50 also permits the second strap 24 to be pivotally moved off of the removable cap 16 allowing the user to remove the cap and gain immediate access to the medicament in the inhaler 30, while leaving the holding means 60 intact. Optionally, the user can gain access to the medicament in the inhaler 30 by lifting up the first strap 58 by its end and in one motion using one hand remove the first strap 58 from the open end of the holster and pivot the second strap 24 off of the removable cap 16. The user can then take off the removable cap 16 from the inhaler 30 to gain access to the medicament in the inhaler.

Having thus described the invention in rather full detail, it will be understood that such detail need not be strictly adhered to but that further changes and modifications may suggest themselves to one skilled in the art, all falling within the scope of the invention as defined by the subjoined claims.

What is claimed is:

1. An inhaler holster comprising:

a. a main body part comprising an elongated sheath having a closed end and an open end;

b. a holding means attached proximal to the open end of said main body part, and extending over the open end to secure an inhaler within the holster wherein said holding means comprises a first strap extending over said open end to secure a hinged cap of a first plastic actuator, said first strap being adapted for releasable engagement with an attachment means disposed longitudinally of said elongated sheath;

c. a grommet affixed to said main body part and positioned off center proximal to the closed end of the sheath, for attaching the inhaler holster to a member passed therethrough.

2. An inhaler holster as recited by claim 1 whereby said attachment means comprises at least one strip of hook and loop fasteners.

3. An inhaler holster as recited by claim 1, wherein said holding means comprises said first strap and a second strap attached to said first strap, and extending over a removable cap comprising a second plastic actuator, said second strap being adapted for releasable engagement with an attachment means disposed longitudinally of said elongated sheath.

4. An inhaler holster as recited by claim 3, whereby said attachment means comprises a plurality of female snap fastener elements disposed on said second strap, and a male snap fastener element fixedly attached to said elongated sheath.

* * * * *